(12) United States Patent
Hick et al.

(10) Patent No.: US 7,820,153 B2
(45) Date of Patent: *Oct. 26, 2010

(54) SEMIOCHEMICAL

(75) Inventors: Alastair James Hick, Great Shelford (GB); John Anthony Pickett, Hitchin (GB); Lester John Wadhams, Harpenden (GB); Johnathan Andrew Napier, Bristol (GB)

(73) Assignee: Plant Bioscience Limited, Norfolk (GB)

( * ) Notice: Subject to any disclaimer, the term of this patent is extended or adjusted under 35 U.S.C. 154(b) by 199 days.

This patent is subject to a terminal disclaimer.

(21) Appl. No.: 10/996,741

(22) Filed: Nov. 24, 2004

(65) Prior Publication Data

US 2005/0147635 A1   Jul. 7, 2005

Related U.S. Application Data

(63) Continuation of application No. 10/149,200, filed as application No. PCT/GB00/04733 on Dec. 11, 2000, now Pat. No. 6,890,525.

(51) Int. Cl.
*A01N 25/00* (2006.01)
*A01N 35/00* (2006.01)
*A01N 27/00* (2006.01)
*A61K 31/12* (2006.01)
*A61K 31/01* (2006.01)
*A61K 31/015* (2006.01)

(52) U.S. Cl. ............... 424/84; 424/405; 514/690; 514/762; 514/763; 514/766; 514/919; 504/348

(58) Field of Classification Search ............... 424/84; 514/690, 762, 763, 766, 918, 919; 504/348
See application file for complete search history.

(56) References Cited

U.S. PATENT DOCUMENTS

| 5,436,226 A | 7/1995 | Lulai et al. | 504/291 |
|---|---|---|---|
| 5,665,344 A | 9/1997 | Pair et al. | 424/84 |
| 6,190,652 B1 | 2/2001 | Pair et al. | 424/84 |
| 6,890,525 B2 * | 5/2005 | Hick et al. | 424/84 |

FOREIGN PATENT DOCUMENTS

| WO | WO 91/18512 A1 | 12/1991 |
|---|---|---|
| WO | WO 9118512 A1 * | 12/1991 |
| WO | WO 94/12029 A1 | 6/1994 |
| WO | WO 97/10703 A1 | 3/1997 |
| WO | WO 98/00023 A2 | 1/1998 |
| WO | WO 98/00023 A3 | 1/1998 |
| WO | WO 00/05964 A1 | 2/2000 |
| WO | WO 01/00026 A1 | 1/2001 |
| WO | WO 01/41568 A3 | 6/2001 |

OTHER PUBLICATIONS

Birkett et al., "New roles for cis-jasmone as an insect semiochemical and in plant defense", PNAS, vol. 97, No. 16, pp. 9329-9334 (2000).*

Smart et al., Journal of Chemical Ecology (2000), vol. 26, No. 4, pp. 1051-1064.*

Agelopoulos, N., et al., "Exploiting semiochemicals in insect control," *Pesticide Science*, Mar. 1999, 55(3), 225-235, XP002164173; ISSN: 0031-613X, Elsevier Applied Science Publisher, Barking, GB.

Birkett, M.A., et al., "New roles for *cis*-jasmone as an insect semiochemieal and in plant defense," Proceedings of the National Academy fo Sciences of the United States of America, Aug. 1, 2000, 97, 9329-9334, XP002164175, Accession No. prev200000438426, *Database Biosis [Online] Bioscience Information Service*, Phila, PA.

Fath, R.A., et al., "Volatile components of *Acacia* sp. Blossoms," J. Agric. Food Chem., 1983, 31(6), 1167-1170, XP002057549, Abstract No. 172845, *Chemical Abstracts*, Columbus, Ohio, vol. 99, No. 21.

Koch, T., et al., "Biosynthesis of *cis*-jasmone. A pathway for the inactivation and the disposal of the plant stress hormone jasmonic acid to the gas phase?," *Chemical Abstracts* Columbus, Ohio, Jan. 5, 1998, 127(1), XP002057552, Abstract No. 366208.

Loughrin, J.H., et al., "Diurnal cycle of emission of induced volatile terpenoids by herbivore-injured cotton plants," Proc. Natl. Acad. Sci. USA, 1994, 91(25), XP002057555, Abstract No. 76939, *Chemical Absttracts*, Columbus, Ohio.

Loughrin, J.H., et al., "Attraction of Japanese beetles (*Coleoptera: Scarabacidae*) to host plant volatiles in field trapping experiments," Environ. Entomol., 1998, 395-400, retrieved from STN-International, XP002164174, Accession No. 129:64289 CA, *Database Chemabs [Online] Chemical Abstracts Service*, Columbus, Ohio.

Novak, G., "Biosynthesis of jasmone," *Chemical Abstracts*, Columbus, Ohio, Sep. 3, 1973, 79(9), XP002057553, Abstract No. 53597.

Raguso, R.A., et al., "Electroantennogram responses of *Hyles lineata* (Spingidae: Lepidoptera) to volatile compounds from *Clarkia breweri* (Onagraceae) and other moth-pollinated flowers," J Chem. Ecol., 1996, 22(10), 1735-1766, XP002057551, Abstract No. 45169, *Chemical Abstracts*, vol. 126, No. 4, Columbus, Ohio.

Ramachandran, R., et al., "Olfactory sensitivity of two sympatric species of rice leaf folders (*Lepidopters: Pyraladae*) to plant volatiles," J. Chem. Ecol., 1990, 16(9), 2647-2666, XP002057550, Abstract No. 39576, *Chemical Abstracts*, vol. 114, No. 5, Columbus, Ohio.

Schlotzhauer, W.S., et al., Volatile constituents from the flowers of Japanese honeysuckle (*Lonicera japonica*), J. Agric. Food Chem., 1996, 44(1), 206-209; XP002057548, Abstract No. 23889, Chemical Abstracts, vol. 124, No. 3.

(Continued)

*Primary Examiner*—Johann R Richter
*Assistant Examiner*—Luke E Karpinski
(74) *Attorney, Agent, or Firm*—Pepper Hamilton LLP

(57) ABSTRACT cis-Jasmone has been discovered to be useful as a semiochemical that changes the behavior of insects and/or the physiology of plants. It has direct signalling roles with plant-feeding aphids, in attraction of aphid predators and parasitoids, and may act as an airborne signal inducing production of volatile plant semiochemicals, including the monoterpene (E)-β-ocimene, that stimulate foraging by parasitoids. It is an extremely benign compound having, to human beings, a pleasant aroma and gives a long-lasting effect after removal of the stimulus.

3 Claims, 3 Drawing Sheets

OTHER PUBLICATIONS

Yoshiara, T., et al., "Potato tuber-inducing substance," *Chemical Abstracts*, Columbus, Ohio, Oct. 8, 1990, 113(15), XP002057554, Abstract No. 129467.

Yukimune, Y., et al., "Methyl jasmonate-induced overproductive of paclitaxel and baccatin III in Taxus cell suspension cultures," *Biological Abstracts*, vol. 96, 1 page, XP002057547, Abstract No. 467116.

Birkett et al., "New roles for cis-jasmone as an insect semio-chemical and in plant defense," PNAS 97(16):9329-9334 (2000).

* cited by examiner

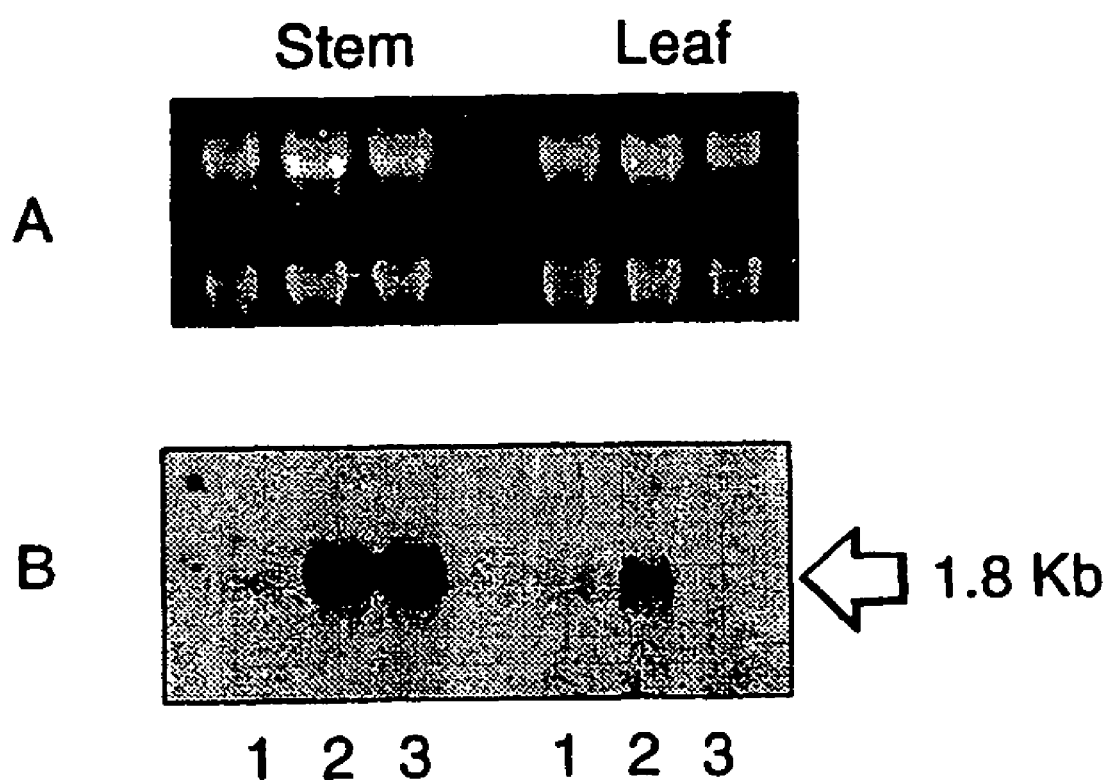

SEMIOCHEMICAL

CROSS-REFERENCE TO RELATED APPLICATIONS

This application is a continuation of U.S. Ser. No. 10/149,200 filed Oct. 15, 2002, now U.S. Pat. No. 6,890,525 which is the U.S. National Stage filing of International Application Serial No. PCT/GB00/04733 filed Dec. 11, 2000, which claims priority to GB 9929309.4 filed Dec. 10, 1999 and to GB 0000329.3 filed Jan. 7, 2000.

FIELD OF THE INVENTION

This invention relates to a new use of a material as a semiochemical, for example a plant stress signal, and to a method of changing the behaviour of insects and/or the physiology of plants comprising the exposure of the insects or plants to this material.

BACKGROUND OF THE INVENTION

Methyl salicylate has been reported as repelling the black bean aphid, *Aphis fabae*, and cereal aphids including the grain aphid, *Sitobion avenae*, and also inhibiting attraction to their host plants. See *J. Chem. Ecol.* 20, 2565-2574 (1994) (Pettersson et al.) and *J. Chem. Ecol.* 20, 2847-2855 (1994) (Hardie et al.). It was suggested that this repellency arose from the relationship of methyl salicylate with salicylic acid and inducible plant defense mechanisms, with the metabolite methyl salicylate acting as a volatile and thereby external signal; the presence of methyl salicylate signalled that chemical defense was induced, and the otherwise attractive host plants were thus perceived as unsuitable hosts by the aphid pests.

More recently, it has been shown that methyl salicylate also acts as an airborne signal mediating plant pathogen resistance. See *Nature* 385, 718-721 (1997) (Shulaev et al.). Methyl salicylate was initially identified by Pettersson et al. as an aphid semiochemical (for example a behaviour-controlling chemical or a signal otherwise influencing the physiology of the organism) by gas chromatography (GC) coupled directly to a single cell recording (SCR) from the olfactory organs on the antenna. Subsequently, more than thirty species of insects, both plant-feeders and their natural enemies, from four orders have been found to possess highly specific and sensitive olfactory receptors for this compound.

WO-A-91/19512 (Washington State University Research Foundation) discloses a method of inducing plant defense mechanisms using jasmonic acid or its esters, or substituted derivatives thereof. The compound induces the production of plant defense proteins, such as proteinase inhibitors, and can promote insect, pathogen or viral resistance in plants by inducing the expression of plant defense genes. Plants may be contacted with the compound by direct application to plant tissue or by airborne transmission of the compound. The expression of plant defense proteins is useful in protecting the plants from the effects of insect attack, but does not prevent the insects in question from attacking the plants. The plants, together with any adjacent plants, will continue to be attacked by predators. The effect moreover is generally short-lived and disappears after removal of the stimulus.

Jasmonic acid and methyl jasmonate, along with a number of other materials, are also discussed by Karban and Baldwin in *Induced Responses to Herbivory* 12-46 (The University of Chicago Press, Chicago, 1997).

Another material, cis-jasmone, is well known as a volatile component of plants and its release can be induced by damage, for example during feeding on cotton by lepidopterous larvae. See *J. Chem. Ecol.*, 21, 1217-1227 (1995) (Loughrin et al.). It is a fragrant material and has often been used for this desirable property. U.S. Pat. No. 4,788,164 (Che et al./Hoechst Celanese Corporation) discloses a sustained release composition including a fragrance or an insect repellent. One example (example IV) uses a solution containing jasmone to impart the odour of jasmine.

U.S. Pat. No. 5,665,344 (Pair et al./The United States of America as represented by the Secretary of Agriculture) indicates that compositions of cis-jasmone were found to attract adult *Lepidoptera*. The cis-jasmone may be used alone or in combination with one or more other volatiles of the Japanese honeysuckle flower, particularly linalool and/or phenyl-acetaldehyde. By attracting the adult *Lepidoptera* to attracticidal baits and/or field traps, the attractants are said to be useful for the control and monitoring of these agricultural pests. The cis-jasmone may be combined with an insect toxicant or pesticide to kill these pests.

We have now discovered that cis-jasmone also has direct signalling roles with plant-feeding aphids, in attraction of aphid predators and parasitoids, and as an airborne signal inducing production of volatile plant components, including the monoterpene (E)-β-ocimene, that stimulate foraging by parasitoids. This signalling role is qualitatively different from that of the biosynthetically related methyl jasmonate and gives a long-lasting effect after removal of the stimulus. In contrast to what the prior art suggests, it may be used to attract insects which are beneficial to the plants concerned or to repel undesirable insects.

SUMMARY OF THE INVENTION

Thus according to the present invention there is provided the use of cis-jasmone as a semiochemical that changes—
  the behaviour of insects by acting as an attractant for beneficial insects and/or repellent of undesirable insects; and/or
  the physiology of plants.

A semiochemical may be regarded as a chemical signal causing a behavioural change or some other physiological change but without generally being directly involved in that process.

The invention may involve the use of cis-jasmone as a plant stress signal or otherwise, and is particularly applicable when cis-jasmone is used on plants so as to cause insect repellency or attractancy. However, cis-jasmone may also be used alone and still cause insect repellency or attractancy. The terms "beneficial" and "undesirable", when used in connection with insects, indicate either their desirability to man or, when the cis-jasmone is used on plants, their desirability to the plant concerned. However, when the cis-jasmone is used on plants to change the physiology of those plants, the invention is not restricted to the ability of the compound to attract beneficial insects or repel undesirable insects.

cis-Jasmone may be used as a repellent of plant-feeding insects, such as plant-feeding aphids. It is however particularly useful as an attractant of beneficial insects, including insect predators and insect parasitoids, especially predators or parasitoids of plant-feeding aphids. It may also, by signifying a plant under stress, encourage some herbivores to attack the apparently weakened plant.

cis-Jasmone may be used to induce the production of volatile plant semiochemicals, such as (E)-β-ocimene, (E,E)-α-farnesene, (−)-β-caryophyllene and (E)-4,8-dimethyl-1,3,7- nonatriene. We have found that (E)-β-ocimene is particularly prevalent following exposure of plants to cis-jasmone, especially when it is used to induce the production of volatile semiochemicals from bean plants.

In a further aspect of the invention, we provide a method of changing— the behaviour of insects by acting as an attractant for beneficial insects and/or repellent of undesirable insects; and/or the physiology of plants;

comprising the exposure of the insects or plants to cis-jasmone.

The cis-jasmone may be applied direct to plant tissue by foliar application, but preferably plants are exposed to air containing cis-jasmone. The cis-jasmone is used at a concentration of 10-1000 μg per litre of air, but particularly favourable results are obtained when the cis-jasmone is used at a concentration of 50-200 μg per litre of air, more particularly 75-125 μg per litre of air and especially in the region of 100 μg per litre of air. This might be achieved by putting the cis-jasmone in an encapsulated form for aerial release.

The cis-jasmone may lead to the repelling or attraction of insects to the plants, for example the repelling of plant-feeding insects such as asphids. It is particularly useful when it leads to the attraction of insect predators or insect parasitoids, especially predators or parasitoids of plant-feeding aphids. This signal would be of immense value for the many areas in which it would be preferable to regulate gene expression, i.e. switch genes on, for the various requirements of crop protection, nutrition or yield timing. Attention may be drawn to the book, *Induced Responses to Herbivory* (The University of Chicago Press, Chicago, 1997) by Karban and Baldwin, where the need for plant-defense inducing signals such as that forming the subject of the present invention is emphasized. Using a signal will result in plant energetics not being wasted. Problems with pest resistance would be obviated by useful genes only expressing their products when required.

Thus, the invention includes the use of cis-jasmone as a semiochemical that changes the behaviour of insects and/or the physiology of plants, wherein the cis-jasmone is used to effect gene expression.

-BRIEF DESCRIPTION OF THE DRAWINGS

In order that the invention may be better understood, it will now be described with reference to the following drawings in which

FIG. 4. shows differential expression of a gene-specific sequence (D251) in *Vicia faba* plants. Total RNA was isolated from stem or leaf tissue of plants exposed to air, methyl jasmonate or cis-jasmone. 10 μg RNA per sample was loaded and separated on a formaldehyde gel (Panel A). The samples were then transferred to a nylon membrane and probed with the D251 sequence (Panel B). Lane 1=air treatment (control); lane 2=cis-jasmone treatment; lane 3=methyl jasmonate treatment. In the case of RNA isolated from leaf tissue, only cis-jasmone treatment results in upregulation.

Figure 1:
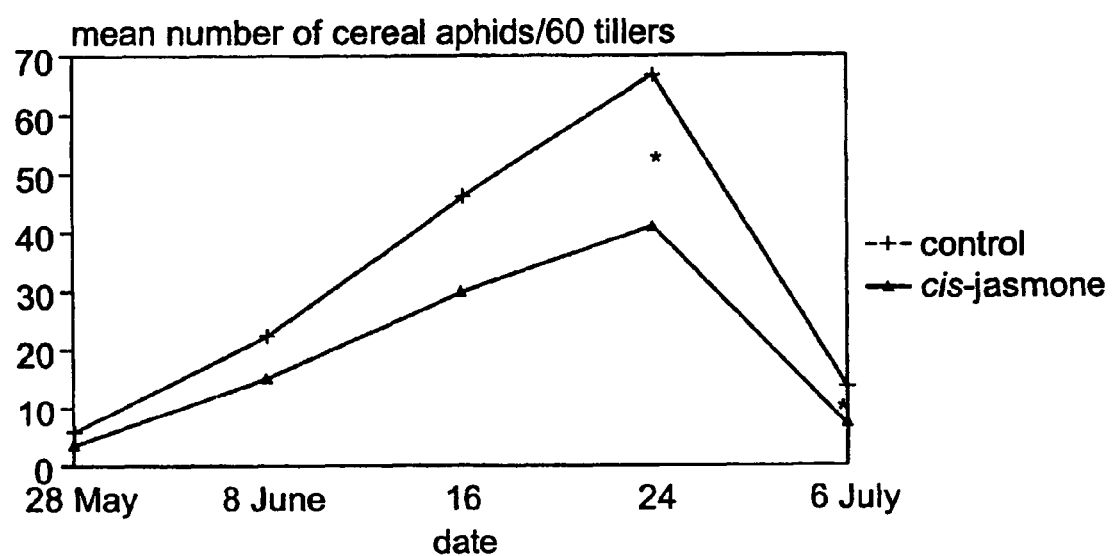
FIG. 1 shows back transformed mean numbers of cereal aphids per 60 tillers of winter wheat, *Triticum aestivum*, following treatment with cis-jasmone on 5 May and 11 Jun. 1999, with an asterisk (*) denoting significant difference between treatments.

DESCRIPTION OF EMBODIMENTS cis-Jasmone was investigated for behavioural activity with the alate forms of the lettuce aphid *Nasonovia ribis-nigri* (*Homoptera*: Aphididae) in a 4-way olfactometer, and was found to be significantly repellent (the mean number of entries into the treated arm was 2.0±0.58, whereas the mean number of entries into the control arms was 4.3±0.58; the mean time spent in the treated arm 0.5±0.16 minutes, whereas the mean time spent in the control arms was 2.1±0.36 minutes; P=<0.05). Repellency was also demonstrated in preliminary field trials with summer morphs of the hop aphid, *Phorodon humuli*, where catches in water traps with visual (yellow) attractancy were reduced by 40% (P<0.04) through a slow release of cis-jasmone (2.05 μg/day/trap).

Field-trapping experiments were also conducted using cis-jasmone against pollen beetles. Attractive yellow bowl traps, at 1 m height and 10 m spacing, were placed in a Latin square design (one row of the Latin square=one replicate; traps are re-randomized to the next row of the square when a mean of 10 beetles are caught per trap). Catches in an unbaited bowl were compared with those bowls baited with cis-jasmone released at two different rates. Analysis was by ANOVA, on transformed total catch data. The transformation used was $x=\log_{10}(y+1)$, where x and y are the transformed and untransformed data, respectively. Transformed means were compared using the LSD (least standard difference) test and transformed back to give the results as set out in Table 1.

TABLE 1

Field-trapping experiments using *cis*-jasmone against pollen beetles.

| | Back-transformed mean catch per replicate | | |
|---|---|---|---|
| | Experiment A | Experiment B | Analysis A |
| unbaited trap | 48.3$^a$ | 333.1$^a$ | 127.3$^a$ |
| *cis*-jasmone 2.2 mg/day | 38.2$^{ab}$ (21%) | 130.7$^{bc}$ (60%) | 70.9$^b$ (44%) |
| *cis*-jasmone 25 mg/day | 31.4$^b$ (35%) | 84.6$^c$ (75%) | 51.7$^c$ (59%) |

The means in the same column, followed by different letters, are significantly different. P<0.05. Numbers in brackets are the percent reduction in trap catch compared with the unbaited trap.

FIG. 1 shows the comparison of mean numbers of cereal aphids on cis-jasmone treated and untreated plots in field studies on five sampling dates. The data have been transformed back from the logs to ease presentation. Aphid numbers were consistently lower in the cis-jasmone plots and differed significantly from the control on the last two sample dates. The predominant aphid species was *Metropolophium dirhodum*, the rose-grain aphid. *S. avenae* and *Rhopalosiphum padi* were also present, but numbers were very low. Numbers of parasitized aphids were also low and no significant difference was observed between treatments.

Since semiochemicals acting as repellents or inhibitors of host attractancy for herbivorous insects are often involved in predation or parasitism, the activity of cis-jasmone was also investigated at higher trophic levels. Thus, the seven-spot ladybird, Coccinella septempunciata (Coleoptera: Coccinellidae), an important aphid predator, was shown to be attracted to a source of the compound in the olfactometer (the mean number of observations in the treated arm was 4.1±1.55, whereas the mean number of observations in the control arms 2.4±0.69; P=<0.005). Responses of the aphid parasitoid Aphidius ervi (Hymenoptera: Braconidae), which preferentially attacks aphids colonizing plants in the Fabaceae, were also investigated in a wind tunnel and demonstrated that cis-jasmone was attractive in a single choice test (Table 2). These experiments indicate a behavioural role for cis-jasmone in influencing interactions between plants, herbivorous insects and their predators and parasitoids.

TABLE 2

Responses of A. ervi in the wind tunnel to synthetic compounds (10 μg) on filter paper (single choice test).

| Stimulus | No. parasitoids tested | % showing oriented flight |
| --- | --- | --- |
| cis-jasmone | 64 | 53.1[a] |
| (E,E)-α-farnesene | 70 | 60.9[a] |
| (E)-β-ocimene | 61 | 48.8[a] |
| hexane control | 45 | 26.7[b] |

ANOVA analysis F=16.19, P=<0.01. Values followed by a different letter are significantly different at P=<0.05 (Tukey multiple comparison test).

Figure 2:
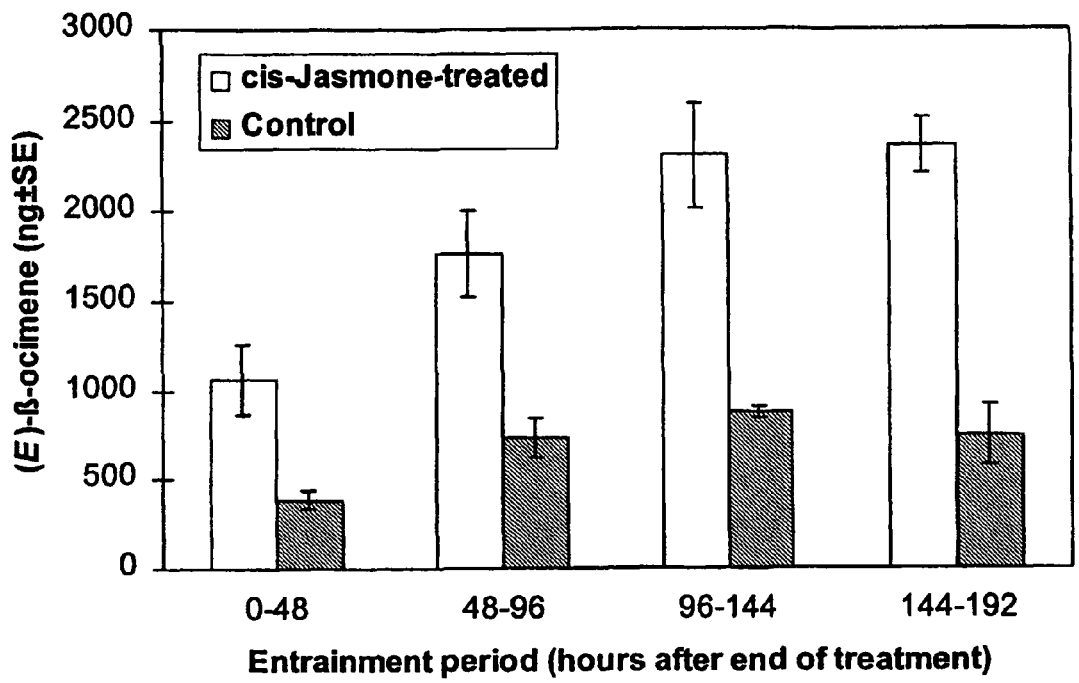
FIG. 2 shows levels of (E)-β-ocimene produced by bean plants, *Vicia faba* (Fabaceae), during 48 hour entrainments following 24 hour exposure to cis-jasmone (100 μg/l in air)

A possible role for the compound as an airborne plant signal was investigated using the broad bean, V. faba (cv The Sutton). Plants were kept for 24 hours in clean air or in air incorporating cis-jasmone at 100 μg/l; subsequently, samples of volatiles released by the plants were obtained by entrainment over 4 periods of 48 hours, i.e. up to 192 hours after the end of the treatment. The cis-jasmone itself was undetectable after 48 hours. However, levels of (E)-β-ocimene released by the plants exposed to cis-jasmone increased significantly over the 192 hour entrainment period and, in all 4 samples, were 2½-3 times higher than those from the control plants (FIG. 2). There was also, from some replicates, enhancement of (E,E)-α-farnesene, (−)-β-caryophyllene and (E)-4,8-dimethyl-1,3,7-nonatriene. These compounds have all been implicated in herbivorous insect-induced production and increased parasitoid foraging. The nonatriene can also be produced innately by plants imitating damage for defense against herbivores and which are thus attractive to parasitoids. (E)-β-Ocimene and (E,E)-α-famesene were investigated with A. ervi in the wind tunnel and both compounds proved to be attractive in the single choice test (Table 2). This activity, and the elevated levels of these compounds produced by V. faba after treatment with cis-jasmone, suggested that there might be increased foraging and attraction of A. ervi to the treated plants compared with the controls. Indeed, in the single choice test, V. faba plants taken 48 hours after treatment, when cis-jasmone levels were undetectable, were significantly more attractive to A. ervi in the wind tunnel than untreated plants (Table 3a). Furthermore, a wind tunnel experiment in which A. ervi were offered a choice of treated or untreated plants demonstrated that over 3 times as many parasitoids oriented towards the cis-jasmone treated plant compared to the control (Table 3b).

TABLE 3

Responses of A. ervi in the wind tunnel to V. faba plants 48 hr after exposure to cis-jasmone (100 μg/l in air).

(a) Single choice test

| Plant treated with | No. parasitoids tested | % showing oriented flight |
| --- | --- | --- |
| cis-jasmone | 50 | 44 |
| hexane control | 50 | 20 |

$\chi^2$ = 6.62 (contingency test using Pearson on Genstat). P = <0.01.

(b) Dual choice test (treated plant versus control plant)

| | % oriented to | |
| --- | --- | --- |
| No. parasitoids tested | treated plant | control plant |
| 50 | 32 | 10 |

$\chi^2$ = 5.762 ($\chi^2$ test). P = <0.05

Figure 3:
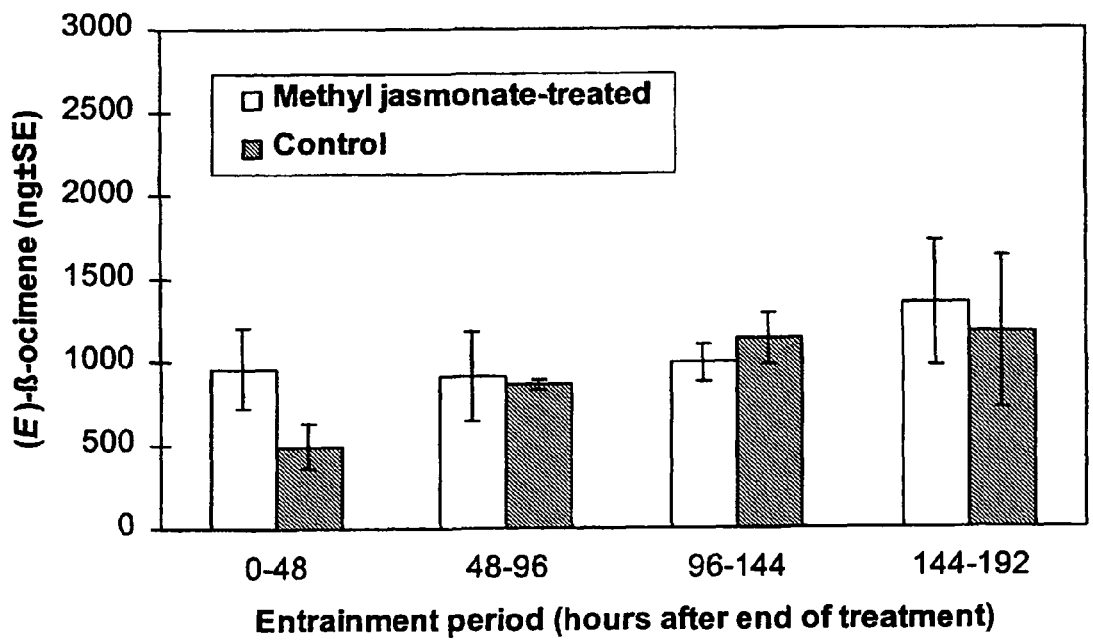
FIG. 3 shows for comparison levels of (E)-β-ocimene produced by *V. faba* during 48 hour entrainments following 24 hour exposure to methyl jasmonate (100 μg/l in air)

We also investigated the activity of methyl jasmonate with V. faba under the same conditions as for cis-jasmone. In this system, exposure to methyl jasmonate did not significantly increase the levels of (E)-β-ocimene released (FIG. 3). This demonstrates that cis-jasmone, as an airborne signal, has properties different to those of methyl jasmonate. cis-Jasmone is closely related to jasmonic acid, being the product of further catabolization, i.e. β-oxidation, dehydration and decarboxylation, although the exact route is not yet reported. The results show that, rather than cis-jasmone being considered as merely another lipoxygenase-derived volatile and a sink for jasmonic acid, it should be viewed as a potentially important airborne plant signal relating to other aspects of plant signalling. It should also be noted that cis-jasmone is more volatile than methyl jasmonate and, as such, could make a more effective signal compound. We have demonstrated that, far from being biologically inactive, cis-jasmone has activity at all three trophic levels investigated in this study.

We have therefore identified a compound capable of inducing production of these types of compounds as an airborne signal, namely cis-jasmone, an extremely benign compound having, to human beings, a pleasant aroma.

METHODS

Examples

Electrophysiology

Electroantennogram (EAG) recordings from alate N. ribisnigri were made using Ag—AgCl glass electrodes filled with saline solution, as reported in J. Exp. Biol. 51, 71-97 (1969) (Maddrell) but without the glucose. The insect was anaesthetized by chilling and the head was excised and mounted on the indifferent electrode. The tip of the recording electrode was removed so that its inside diameter was just wide enough to accept the terminal process of the antenna. The signals were passed through a high impedance amplifier (UN-03b, Syntech) and displayed on an oscilloscope.

Coupled Gas Chromatography (GC)-Electrophysiology

The coupled GC-electrophysiology system, in which the effluent from the capillary column GC is delivered simultaneously to the antennal preparation and the GC detector, has been described previously. See Wadhams in Chromatography and *Isolation of Insect Hormones and Pheromones* (eds. McCaffery et al.) 289-298 (Plenum Press, New York, 1990). Separation of the air entrainment sample was achieved on an AI 93 GC equipped with a cold on-column injector and a flame ionization detector (FID). The column (30 m×0.53 mm ID, HP-1) was maintained at 40° C. for 2 min and then programmed at 10° C./min to 250° C. The carrier gas was hydrogen. The outputs from the EAG amplifier and the FID were monitored simultaneously on a chart recorder.

Olfactometry: Aphids

Behavioural assays were done in a Perspex™ olfactometer similar to that described in *J. Entomol. Scand* 1, 63-73 (1970) (Pettersson), with a weak airstream directed towards the centre from each of 4 side arms. The test compound (1 µg) in hexane (10 µl) was placed on filter paper (Whatman No. 1) at the end of one of the side arms, with hexane alone used as a control in the other arms. One alate virginopara of *N. ribisnigri* was placed in the centre of the arena and its movements observed over 10 min. The apparatus, maintained at 24° C., was lit from above by fluorescent tubing and was rotated 90° every 2.5 min to avoid any directional bias. The experiment was replicated 6 times and results analysed by Student's t-test.

Olfactometry: Ladybirds

Apparatus and methodology were similar to that employed for aphids (above). The test compound was applied in 0.5 µl microcaps (Drummond Sci. Co.) at the end of one of the side arms and each arm was supplied with moist filter paper to minimize differences in relative humidity. Individual *C. septempunctata* were introduced into the centre of the arena and their positions noted every 2 min for 20 min. The experiment was replicated 8 times and results analysed as above.

Wind Tunnel Studies

Naive female *A. ervi* were flown in a wind tunnel, as described in *J. Chem. Ecol.* 16, 381-396 (1996) (Poppy et al.). The parasitoids were released 25 cm downwind (single choice tests) or 40 cm downwind (dual choice test) of the target, which was either a plant or a synthetic compound (10 µg in 10 µl hexane) placed on a 2×1 cm strip of filter paper (Whatman No. 1) surrounded by a ring of green crepe paper. The proportions of parasitoids responding with an oriented flight to the synthetic chemicals were calculated each day on 3 separate days. These values were then subjected to a logit transformation to normalize the data before being analysed by ANOVA followed by Tukey post-hoc tests. The number of parasitoids orienting upwind to the single plant target were recorded and subjected to a $\chi^2$ contingency test (Pearson method on Genstat—see Genstat 5 Committee. *Genstat 5 Reference Manual, Release* 3 (Clarendon Press, Oxford, 1993)) to determine whether an orienting response was linked to the type of plant treatment. The numbers orienting to each plant in the dual choice test were analysed by a $\chi^2$ to determine whether one plant was more attractive than the other.

Field Studies

Plots (6 m×6 m) of winter wheat, *Trilicum aestivum* (cv Consort), were arranged in a 5×5 quasi-complete Latin square design. The five cis-jasmone treated plots were sprayed on 5 May and 11 Jun. 1999, using a hand-held hydraulic device, at a rate of 50 g active ingredient/ha in 200 l/ha of aqueous Ethylan BV (0.1%). Control plots were untreated. Cereal aphids and parasitized aphids were counted on 8 occasions between early May and mid-July. At each count, five tillers were inspected at 12 separate sites on two diagonal transects totalling 60 tillers per plot. Transformed data ($y=\log(y+1)$) were subjected to ANOVA and the sums of squares of the treatments were partitioned to test for significant differences.

Induction Studies

Bean plants, *V. faba* (cv The Sutton) were grown under standard glasshouse conditions until the 2-4 leaf stage when they were rinsed free of soil and transplanted into baked glass jars containing washed sand, with 3 plants per jar. These were left for 1-2 days to acclimatize. Plants to be treated (three jars of three plants each) were sealed in a 25 l glass tank for 24 hours with either cis-jasmone or methyl jasmonate (2.5 mg) applied to a piece of filter paper (Whatman No. 1) placed on the floor of the tank. Treated or untreated plants were then placed in 10 l glass entrainment vessels and the volatiles from each collected over 48 hour periods for 192 hours. See Blight in *Chromatography and Isolation of Insect Hormones and Pheromones* (eds. McCaffery et al.) 289-298 (Plenum, New York, 1990). Volatiles were eluted from glass tubes containing Porapak Q (50 mg), using freshly distilled diethyl ether (500 µl), and then concentrated to 100 µl for analysis by GC and GC-MS.

Analysis

GC analysis was carried out using a Hewlett Packard 5890 GC equipped with a temperature programmable on-column injector and FID. This was fitted with HP-1 (50 m×0.32 mm ID) and SPB-35 (30 m×0.32 mm ID) columns with hydrogen as the carrier gas. The oven was maintained at 40° C. for 1 min then programmed at 10° C./min to 250° C. GC-MS analysis was carried out using a Hewlett Packard 5890 GC connected to a VG Autospec mass spectrometer (Fisons Instruments). Ionization was by electron impact at 70 eV, 230° C. The GC was maintained at 30° C. for 5 min then programmed at 5° C./min to 180° C. Detection limits for cis-jasmone in the entrainment samples were 40 pg/hour for GC and 400 pg/hour for GC-MS. Compounds identified by GC/GC-MS were confirmed by co-injection of authentic samples on HP-1 (non-polar) and SPB-35 (polar) columns. Authentic samples were obtained from commercial sources, except for (E)-β-ocimene, (E,E)-α-farnesene and (E)-4,8-dimethyl-1,3,7-nonatriene which were synthesized by standard methods, as follows.

(E,E)-α-Farnesene and (E)-β-ocimene (E,E)-α-Farnesene and (E)-β-ocimene were synthesized from 3-methyl-2,5-dihydrothiophene-1,1-dioxide. See *J. Chem Soc. Chem. Comm.*, 1984, 1323 (Chou et al.). Sulphur dioxide elimination was achieved using excess lithium aluminium hydride following a modified protocol based on that in *Tetrahedron Lett.*, 1977, 11, 947 (Gaoni).

To a stirred suspension of lithium aluminium hydride (1 equiv. by weight) in refluxing dry diethyl ether (10 mmol/ml) was added dropwise via syringe a solution of the dihydrothiophene-1,1-dioxide (1 equiv.) in dry diethyl ether (1 ml). After refluxing for 1 hour, the cooled (0° C.) mixture was treated with 15% NaOH (1 ml), water (3 ml), and the mixture filtered through Celite™. Evaporation of the filtrate under reduced pressure followed by column chromatography over Florisil (100% hexane) yielded the product as a colourless oil.

4,8-Dimethyl-1,3,7-nonatriene 4,8-Dimethyl-1,3,7-nonatriene was synthesized in two steps from geraniol.

Geraniol (7.0 g, 0.045 mol, 1 equiv.), manganese (IV) dioxide (100.0 g) and dichloromethane (500 ml) were stirred together at ambient temperature overnight. The mixture was filtered through Celite™, and the filtrate concentrated in vacuo to yield geranial (5.42 g, 80%). A cooled (−15° C.), stirred suspension of methyltriphenyl-phosphonium iodide (16.0 g, 0.039 mol, 1.1 equiv.) in tetrahydrofuran (50 ml) and diethyl ether (50 ml) was treated with n-butyllithium (2.5 M; 16 ml, 0.039 mol, 1.1 equiv.). After 0.25 hours, geranial (5.42 g, 0.036 mol, 1 equiv.) was added and the mixture allowed to stir at ambient temperature for 1 hour. The mixture was partitioned between diethyl ether (200 ml), water (200 ml) and petroleum ether b.p. 40-60° C. (200 ml), and the organic layer dried ($MgSO_4$) and concentrated in vacuo to yield a crude oil which was subjected to column chromatography over Florisil (100% hexane) to give the nonatriene as a colourless oil (3.42 g, 64%).

DIFFERENTIAL DISPLAY

In order to determine if cis-jasmone was capable of inducing alterations in plant gene expression, the sensitive technique of differential display was carried out on RNA extracted from plants which had been exposed to air, methyl jasmonate or cis-jasmone. A number of the resulting PCR products were observed to show alterations in their abundance in the presence of cis-jasmone. To confirm this observation, bands of interest were recovered by excision from the dried gel and re-amplified with the appropriate pair of oligonucleotide primers. The resulting PCR products were cloned and sequenced to confirm the homogeneous nature of the amplified product. These sequences were then used to probe RNA isolated from control or treated *V. faba* plants. As can be seen from FIG. 4, one particular sequence (D251) was shown to be upregulated in leaf tissue only in the presence of cis-jasmone. Interestingly, when this same (cloned) sequence was used to probe RNA isolated from *V. faba* stem tissues, it was upregulated to a similar level in plants that had been treated with either cis-jasmone or methyl jasmonate. It is important to note that the nature of the differential display technique generates short gene-specific probes, containing mainly 3' untranslated regions of transcribed sequences, and therefore the functional part of the differentially expressed gene is unknown.

Thus, using differential display and confirmatory northern blotting, we have shown that methyl jasmonate and cis-jasmone have apparently distinct effects on plant gene expression. In this study, the differentially displayed PCR product D251 was cloned and used to probe northern blots from leaf or stem tissues of *V. faba* plants treated with air, methyl jasmonate or cis-jasmone. This clearly showed (FIG. 4) that whilst the D251 sequence was upregulated by treatment with vapours of both compounds in stem tissue, only cis-jasmone brought about an increase in the steady-state transcript level of this sequence in leaf tissue. Thus, the two compounds have distinct effect on plant gene expression and the response to these signalling compounds may be tissue-specific.

The invention claimed is:

1. A method of repelling an insect from a plant comprising exposing the plant and the insect to cis-jasmone, wherein i) the plant is exposed to air containing cis-jasmone at a concentration of about 10 to about 1000 μg per liter of air, or ii) the cis-jasmone is applied directly to plant tissue by foliar application, wherein the insect is chosen from a cereal aphid, a lettuce aphid, a hop aphid, a rose grain aphid, *metropolophium dirhodum, S. avenae, rhapalosiphum padi*, and pollen beetle.

2. The method of claim 1 wherein the cis-jasmone is used at a concentration of about 100 μg per liter of air.

3. The method of claim 1 wherein the plant is wheat, lettuce, hop, or a bean plant.

* * * * *